Figure 1:
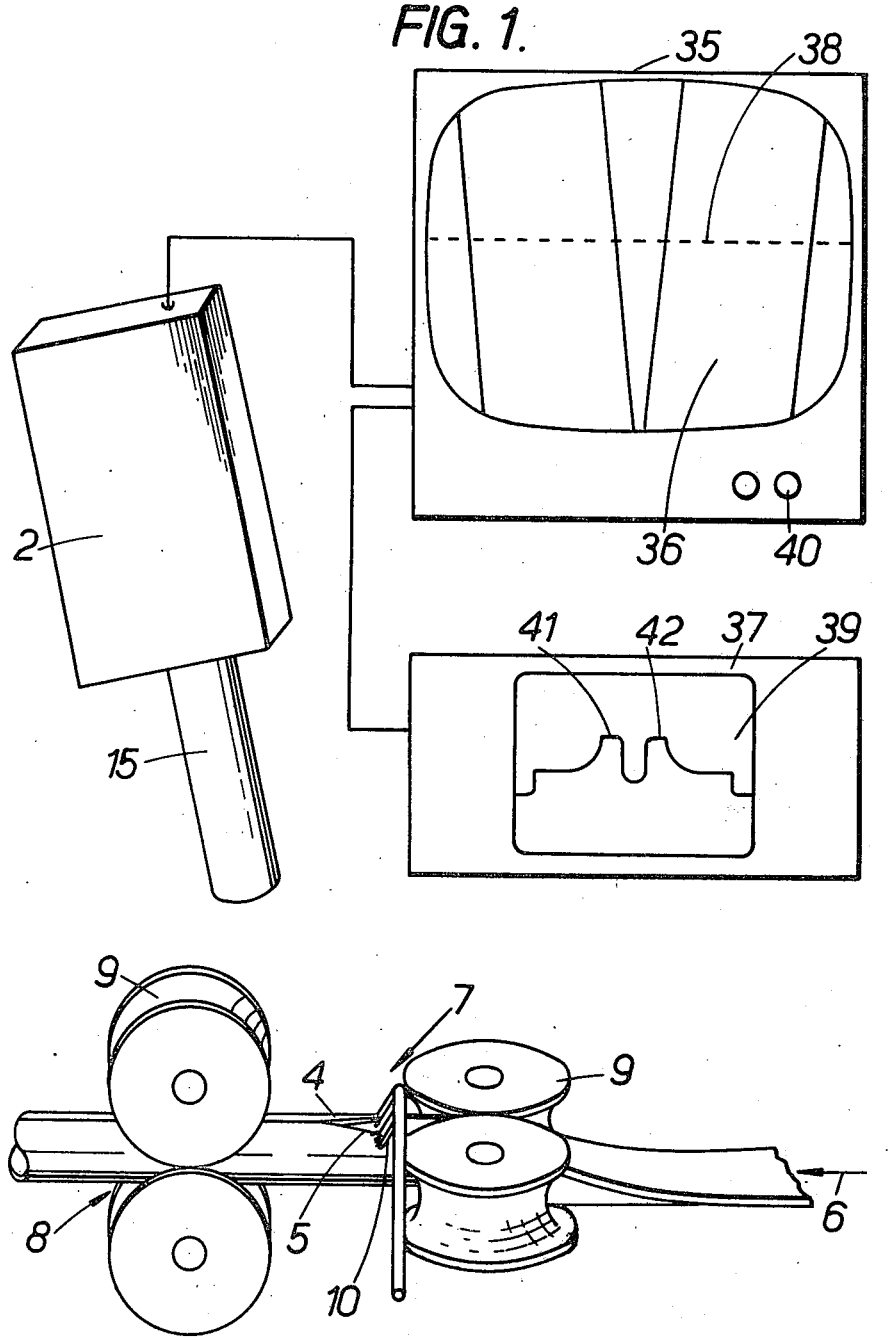

United States Patent [19]
Bosworth

[11] 4,001,497
[45] Jan. 4, 1977

[54] MONITORING OF WELDING

[75] Inventor: Clive James Arthur Bosworth, Kettering, England

[73] Assignee: British Steel Corporation, London, England

[22] Filed: May 24, 1974

[21] Appl. No.: 473,042

[30] Foreign Application Priority Data
June 18, 1973  United Kingdom ............ 28873/73

[52] U.S. Cl. .................................. 358/101; 72/286; 73/340; 73/355 R; 178/DIG. 8
[51] Int. Cl.$^2$ ......................................... H04N 7/18
[58] Field of Search ................. 178/DIG. 8, DIG. 1, 178/6, 8, 6.8; 73/340, 355 R; 72/37, 286, 364, DIG. 12, DIG. 13

[56] References Cited
UNITED STATES PATENTS

| | | | |
|---|---|---|---|
| 3,635,085 | 1/1972 | Shimotsuma | 73/340 |
| 3,707,754 | 1/1973 | Meleka | 72/286 |
| 3,798,366 | 3/1974 | Hunt | 178/DIG. 8 |
| 3,873,830 | 3/1975 | Forster | 73/355 R |

*Primary Examiner*—Howard W. Britton
*Attorney, Agent, or Firm*—Nolte and Nolte

[57] ABSTRACT

The thermal profiles existing across metal surfaces to be continuously welded together (e.g. the longitudinal edges of metal strip which is to be formed into metal tube) are viewed by a television camera just prior to their being welded together and electrical signals from the camera are utilized to produce in a wave form monitor a visual wave-form representation of the thermal profiles existing across the viewed surfaces.

5 Claims, 3 Drawing Figures

MONITORING OF WELDING

This invention relates to a method of and apparatus for monitoring thermal profiles across metal surfaces which are to be welded together in a continuous welding process.

According to the present invention in one aspect, a method of monitoring or controlling thermal profiles across metal surfaces to be welded together in a continuous welding process comprises the steps of viewing by means of a television camera the surfaces just prior to their being welded together, and utilising electrical signals from the camera to produce on a wave-form monitor visual wave-form representations of thermal profiles existing across the viewed surfaces. The wave form monitor may be an oscilloscope.

According to the present invention in another aspect, apparatus for monitoring thermal profiles existing across metal surfaces to be welded together as they pass between heat treatment and welding stages of continuous welding plant, comprises a television camera operable to view the surfaces as they pass between said stages, and a wave-form monitor operable to receive electrical signals from the camera to produce a visual wave-form representation of thermal profiles existing across the viewed surfaces.

The wave-form monitor may comprise an oscilloscope and a cathode ray tube may be located in circuit between the television camera and the oscilloscope, the visual wave-form produced by the oscilloscope being derived from a raster line of the cathode ray tube and applied as an input to the oscilloscope.

The surfaces to be continuously welded together may be longitudinal edges of metal strip which is to be formed into tubes. The longitudinal edges of the strip may be locally heated in the heating zone prior to welding by means of a flow of oxygen. The amount of oxygen supplied to one surface may be varied in relation to that supplied to the other surface to correct any difference in respective temperature indicated by the wave-form displayed by the oscilloscope.

Figure 2:
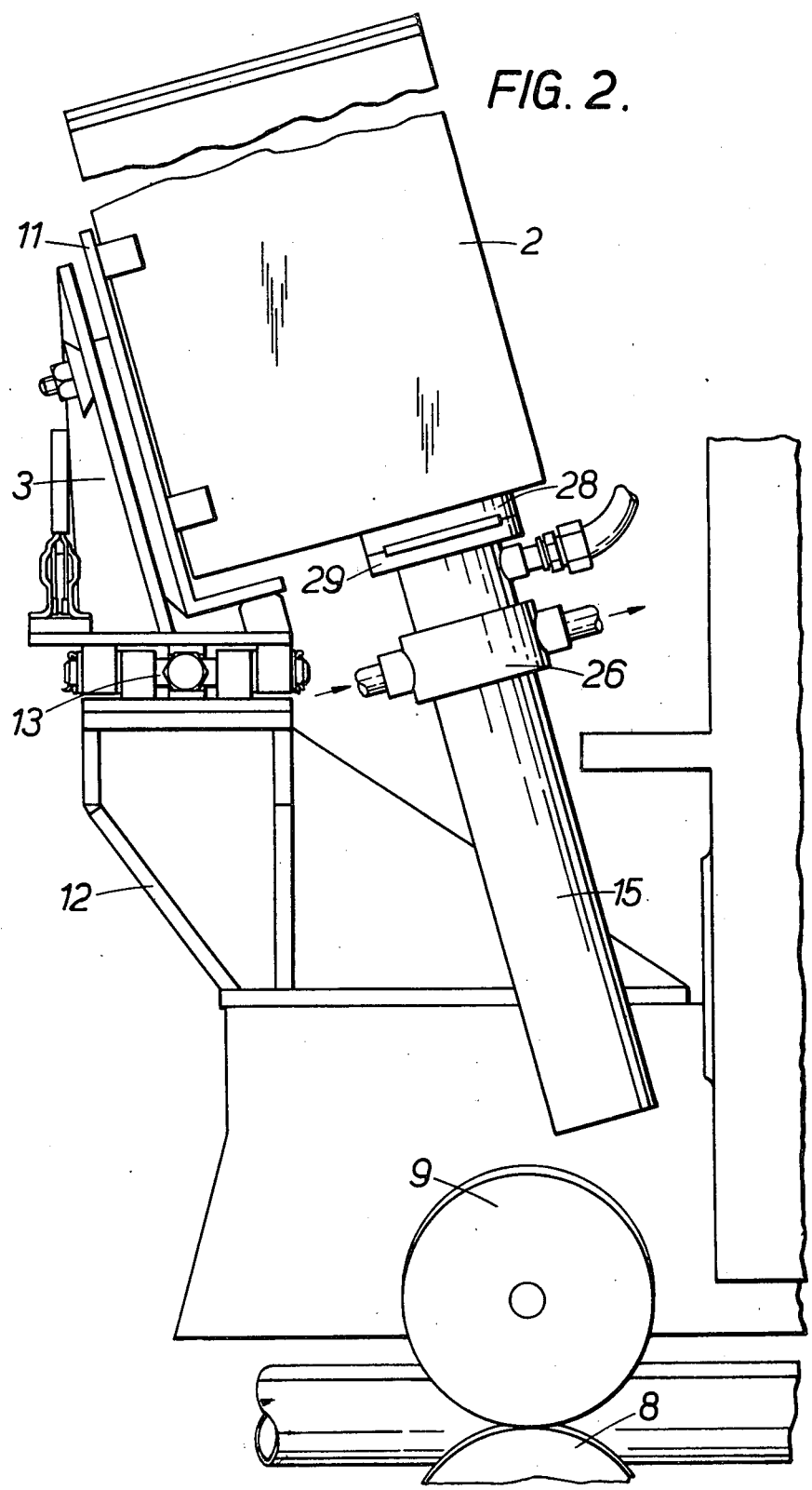
Figure 3:
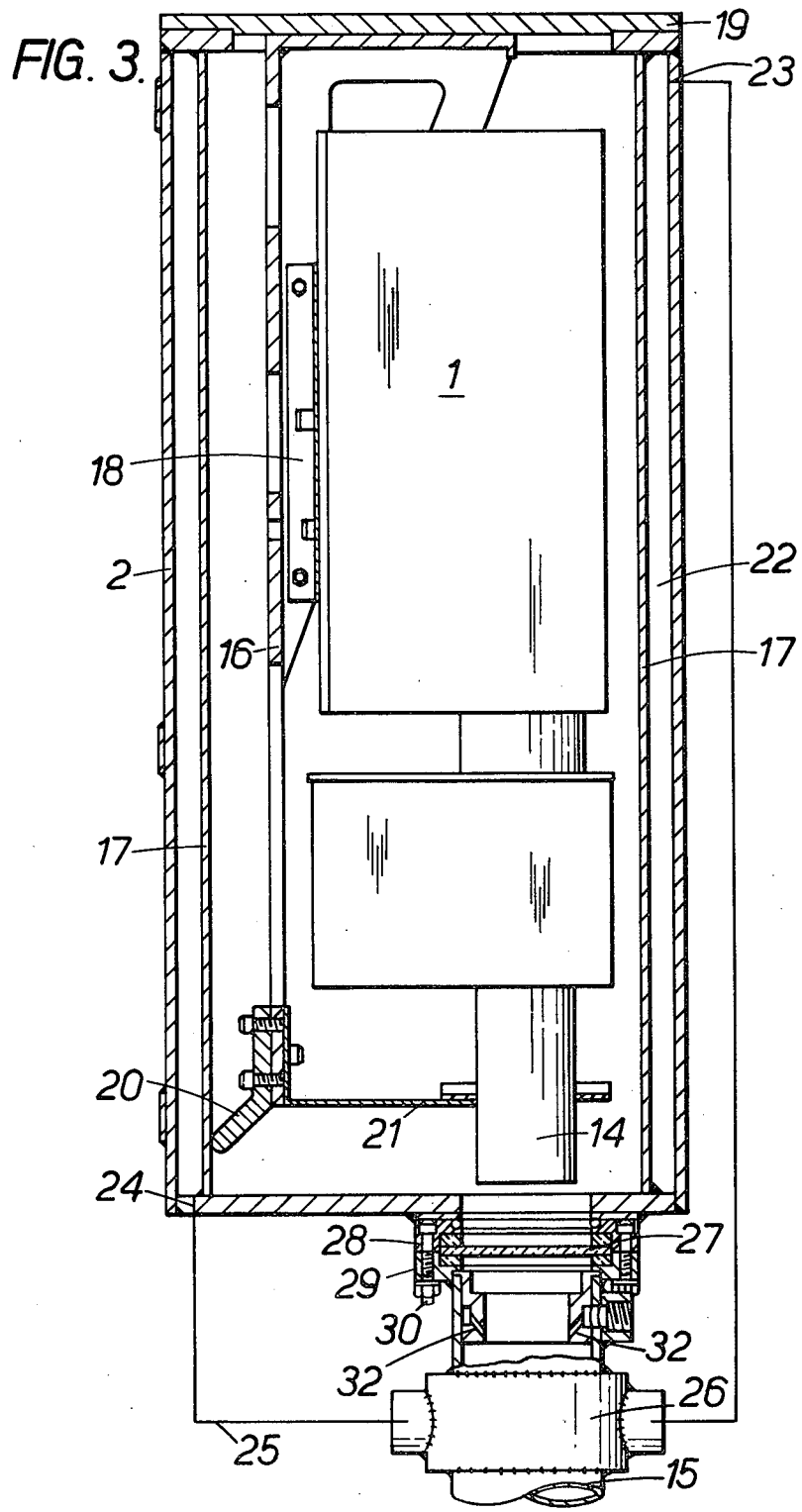

In order that the invention may be more readily understood, one embodiment thereof will now be described by way of example with reference to the accompanying drawing in which:

FIG. 1 diagrammatically illustrates apparatus in accordance with the invention included in plant for continuously welding together the longitudinal edges of metal strip to form tubes;

FIG. 2 is an elevational view of certain features of the apparatus illustrated in FIG. 1; and FIG. 3 is a section taken through a camera housing which forms part of the apparatus illustrated in FIG. 1.

The apparatus illustrated includes a television camera 1 housed within a steel casing 2 which is supported by an assembly 3 above the path taken by the longitudinal edges 4 5 of shaped metal strip as they pass in the direction of arrow 6 from a heating zone 7 to a welding zone 8. The strip is shaped by roller 9 and the edges 4 5 are continuously welded in the zone 8 to form a finished tube. The camera is sighted so that it scans the surfaces 4 5 downstream of the heating zone 7 and immediately upstream of the welding zone 8. In the zone 7, the surfaces 4 5 are spot heated by means of oxygen jets which are directed downwardly onto the surfaces from a nozzle assembly 10. The rate at which oxygen is supplied to the assembly 10 is metered and can be controlled by the process operator. Also, the position of the jet or jets of oxygen relative to the surfaces 4 5 can be changed to vary the relative amounts of oxygen supplied to the respective surfaces.

As will be seen from FIG. 2, the camera casing 2 is supported by a bracket 11 carried by a pillar 12. A pivot bar 13 is interposed between the bracket 11 and the pillar 12 to permit pivotal movement of the casing 2 relative to the assembly 3 and to the metal surfaces to be viewed.

As shown in FIG. 3 the camera 1 is a conventional interlaced television camera fitted with a clear glass heat filter and infra red filter, a lens housing 14 and a sighting tube 15. The focus and iris settings of the camera are adjustable by remote control.

The camera 1 is carried on a base member 16 which is mounted within a cylindrical housing 17. The camera is supported on the base 16 by a mounting 18; resilient members are positioned between the camera 1 and the base 16 to dampen vibrations imparted to the casing 2. The base 16 is welded at one end to the rear face 19 of the casing 2 and is spaced at its other end from the housing 17 by a runner 20. The lens housing 14 of the camera is supported by a collar 21 carried by the base 16. Coolant, normally water, is conveyed through ports 23 24 respectively to and from the annulus 22 defined between the housing 17 and the casing 2. Coolant leaving the annulus 22 via the outlet port 24 is conveyed by piping 25 to a collar 26 which encompasses the upper end of the sighting tube 15. On leaving the collar 26 the coolant may be recirculated via a heat-exchange (not shown) to the inlet port 23.

A removable cover glass 27 is located between abutting flanges 28 29 of, respectively, the casing 2 and the sighting tube 15. Flanges 28 29 are secured together by nuts and bolts 30. The cover glass 27 is provided to protect the lens system from foreign bodies travelling up the tube 15 and can be readily removed to facilitate cleaning of the lens system. Compressed air can be introduced to the sighting tube 15 through inclined passages 32 to deter steam and scale from entering the tube.

Electrical signals from the camera 1 are fed to the cathode ray tube of a picture monitor 35 (FIG. 1) which provides a visual display 36 (which may be in colour) of the outline of the metal surfaces 4 5. An oscilloscope 37 receives from the picture monitor 35 an input signal derived from any one raster line 38 of the cathode ray tube of the monitor, and produces a wave-form visual display 39 of thermal profiles across the surfaces 4 5. Any particular raster line 38 of the cathode ray tube can be selected by means of a dial 40.

In operation, the surfaces 4 5 to be continuously welded together are viewed continuously by the television camera 1 as they pass from the heating zone 7 in which they are heated to a temperature of about 1350° C by the oxygen jets issuing from the nozzle assembly 10, to the welding zone 8.

Electrical signals are fed from the camera 1 to the monitor 35 and there to the oscilloscope 37 to provide the process operator with visual displays of the outline of the surfaces 4 5 and the thermal profiles across these surfaces just prior to the welding zone.

Deviations from the desired attitude of the surfaces 4 5 prior to welding are illustrated on the display 36 and suitable remedial action can be effected by the process operator with the minimum of delay.

The wave-form peaks 41, 42 displayed by the oscilloscope 37 represent the respective temperature surfaces 4 5 and, should one peak fall below the other, the difference in temperature displayed can be corrected by suitable adjustment of the position of the nozzle assembly 10 to increase the oxygen supply to the cooler surface.

In an illustrated embodiment, the wave-form display 39 of the thermal profiles across the surfaces 4 5 is displayed on an unused portion of the picture monitor 35; thus both displays 36 and 39 will appear on one monitor.

It will be appreciated that by means of the embodiments described above, temperature profiles existing at the surfaces to be welded together are monitored and visually displayed in order that suitable countermeasures may be taken to prevent faults in the finished welding.

I claim:

1. In a method of controlling thermal profiles across metal surfaces to be welded together in a continuous welding process, the improvement which comprises the steps of viewing, by means of a television camera, the surfaces just prior to their being welded together and transmitting electrical signals representative of the thermal and visual images of the viewed surfaces from the camera to a cathode ray tube to produce an image of said viewed surfaces, deriving a signal from a raster line of said cathode ray tube and applying that signal as an input to an oscilloscope to produce on said oscilloscope a visual wave form representative of the thermal profile existing across said viewed surfaces, observing said visual wave form and, in response to that observation, controlling heating means applied to said surfaces to adjust said thermal profile to a desired form.

2. The method as claimed in claim 1 wherein the location of said raster line of said cathode ray tube from which said signal is derived is marked on said cathode ray tube whereby the location of said visual wave form relative to said visual image of said cathode ray tube is identified.

3. Apparatus for controlling thermal profiles existing across metal surfaces to be welded together as they pass between heat treatment and welding stages of a continuous welding plant comprising a television camera disposed to view said surfaces as they pass between said stages, a cathode ray tube connected to receive signals from said camera representative of the thermal and visual images of the viewed surfaces, means deriving a signal from a raster line of said cathode ray tube and applying that signal as an input to an oscilloscope to constitute means for producing, on said oscilloscope, a visual wave form representative of the thermal profiles existing across said viewed surfaces, and means at said heat treatment stage operable to vary the thermal profile.

4. Apparatus according to claim 3 wherein the surfaces to be welded together are the longitudinal edges of metal strip which is to be formed into tubular configuration and wherein means is provided for locally heating each longitudinal edge in the heat treatment stage by means of a flow of oxygen.

5. Apparatus according to claim 4, wherein means are provided to vary the amount of oxygen supplied to a surface in relation to that supplied to the other surface.

* * * * *